(12) United States Patent
Hayashi

(10) Patent No.: US 6,210,697 B1
(45) Date of Patent: Apr. 3, 2001

(54) MEDICAMENT FOR HYPOTHERMIA TREATMENT

(75) Inventor: Nariyuki Hayashi, Tokyo (JP)

(73) Assignee: Sumitomo Pharmaceuticals Company, Limited, Osaka (JP)

( * ) Notice: Subject to any disclaimer, the term of this patent is extended or adjusted under 35 U.S.C. 154(b) by 0 days.

(21) Appl. No.: 09/284,649

(22) PCT Filed: Oct. 16, 1997

(86) PCT No.: PCT/JP97/03735

§ 371 Date: Apr. 16, 1999

§ 102(e) Date: Apr. 16, 1999

(87) PCT Pub. No.: WO98/16244

PCT Pub. Date: Apr. 23, 1998

(30) Foreign Application Priority Data

Oct. 16, 1996 (JP) .................................................. 8-295666

(51) Int. Cl.[7] .................................................. A61F 2/02
(52) U.S. Cl. .................................................. 424/423
(58) Field of Search .................................................. 424/423

(56) References Cited

U.S. PATENT DOCUMENTS 5,426,096 * 6/1995 Sonksen et al. .................... 514/12

OTHER PUBLICATIONS

J. Vet. Med. B., vol. 42, No. 1 (1995), p. 12–18.
Journal of Interferon Research, vol. 8, No. 3 (1988), p. 393–402.

* cited by examiner

Primary Examiner—Carlos A. Azpuru
(74) Attorney, Agent, or Firm—Birch, Stewart, Kolasch & Birch, LLP

(57) ABSTRACT

A medicament containing human growth hormone (hGH), which can prevent or decrease the immunosuppression and the onset of infectious diseases such as pneumonia in a hypothermia treatment that has been recognized to show remarkable effects on the lifesaving and/or the improvement of recovery of a patient with serious cerebral injury, and thereby contributing to the expansion of the range of application and the improvement of lifesaving effect of hypothermia treatment.

9 Claims, 2 Drawing Sheets

MEDICAMENT FOR HYPOTHERMIA TREATMENT

This application is the national phase under 35 U.S.C. §371 of PCT International Application No. PCT/JP97/03735 which has an International filing date of Oct. 16, 1997 which designated the United States of America.

TECHNICAL FIELD

The present invention relates to a supportive use of a medicament for carrying out a hypothermia treatment safely, and a pharmaceutical composition to be used in the treatment. More specifically, it relates to a medicament which is used supportively to inhibit the suppression of immune functions or the onset of infectious complications in a mild hypothermia treatment aimed at the prevention of the cerebral perfusion disorder of a patient with serious cerebral injury.

BACKGROUND TECHNOLOGY

The hypothermia treatment is a therapeutic method carried out to prevent an irreversible cranial nerve injury in the cases of accident or angiopathy, which is characterized in that a subject in anesthetized condition is cooled with a blanket having circulating cold water so that the temperature of the spinal cord and central nervous system is kept slightly low (cerebral temperature=ca., 33° C.) for a certain period of time. Clinical application of the treatment was started from about 1994, after the effectiveness was confirmed in the field of animal experimental pharmacology around the latter half of 1980's. Since then, remarkable successes have been reported in cases of severe head injury and subarachnoid hemorrhage (Hayashi, N et al.: J. Cereb. Blood Frow Metab. 15 (Suppl.1): S724, 1995, Maekawa, T et al.: Minerva-Anesthesiol. 60(10): 537–540, 1994).

The hypothermia treatment herein referred to is entirely different from a primitive one that had been employed in the field of thoracic surgery, in which the brain temperature was simply lowered to below 30° C. By contrast, the hypothermia treatment herein described came to afford satisfactory results only after the detailed procedures for controlling the cerebral temperature, blood pressure, respiration, intracranial pressure or the like; preventing stress diseases or infectious diseases; and matters to be regarded while rewarming were established (Hayashi, N., Hirayama, A: Medical Postgraduates 31:59–71,1993).

In the hypothermia treatment, one must pay the greatest attention to a peculiar damage of immune protection system of a living body when the cerebral temperature lowered, and the immunosuppression due to tissue injury or the like while the temperature is kept low and at the time of rewarming (Hayashi, N., "Cerebral Hypothermia" Sogo-Igaku, & Co., May 29, 1995 pp.53). The suppression of immune function could result in the onset of infectious diseases such as pneumonia.

There are certain measures currently taken to maintain the immune function during the hypothermia treatment, for example, the administration of L-glutamine (Glumine™ Kyowa Hakko Kogyou Co., Ltd.) which serves as an energy source for T- or B-cells (DeBiasse MA and Milmore DW: New Horizons 2(2): 122–130, 1994); the administration of y-globulin or opsonin; or the induction of in vivo synthesis of glutamic acid through the electric stimulation of skeletal muscle (Souba WW et al., J. Parenteral and Enteral Nutrition 9(5): 608–617, 1985), but they are not perfectly effective. Accordingly, there are still some cases involved in refractory pneumonia in the absence of sufficient preventive methods.

The extent of damages of tissue functions at the time of lowering/elevating the cerebral temperature, which possibly causes immunosuppression, is suggested to vary depending on the blood hemoglobin level or renal excretion function of patients. Accordingly, the hypothermia treatment is hardly applied to some patients showing suppression of these functions, for example, a patient of renal disease or of old age, because of the above-mentioned risks.

There have not been known any medicines capable of preventing damages of immune protection system specific to hypothermia treatment, or enhancing the damaged immune function effectively. The hypothermia treatment failed to show satisfactory lifesaving effects because of infectious diseases related to immunosuppression and could not be applied widely, notwithstanding that it is expected to show remarkable effect in the lifesaving and/or the amelioration of recovery of patients with serious cerebral injury.

On the other hand, human growth hormone (hereinafter, referred to as hGH) has not only been used in the treatment of pituitary dwarfism, but also known to be effective in the healing promotion of fracture and burn wound and also in the treatment of patients in nutrient malabsorption condition (Nikkei Bio Almanac 94/95). Further, there has been reported that hGH has an immune function potentiation effect or protection effect on tissue injury caused by free radical in vivo (U.S. Pat. No. 5,317,012, Japanese Patent Publication (Kohyo) 6-503320). However, it has never been known or even suggested that hGH has an ability to prevent or reduce the damages of immune protection system of a living body especially the immunosuppression due to peculiar tissue damages in a hypothermic treatment, in particular, when rewarming.

One of purposes of the present invention is to provide a pharmaceutical composition capable of preventing the suppression of immune function, and inhibiting or relieving an infectious disease in connection with a hypothermia treatment, whereby ensuring the safety of the treatment and allowing said treatment to exhibit the excellent preventive effect on the cerebral perfusion disturbance of a patient with serious cerebral injury to the full.

DISCLOSURE OF INVENTION

The present inventors have intensively studied to solve the problems above and found that the blood hGH level decreased as the cerebral temperature lowered and that it became about zero at 32° C. The inventors further found that CD4 and CD8 (leukocyte differentiation antigens), which are indices of cellular immunity function, were recovered by the administration of hGH. Based on these findings, the present inventors then confirmed that the administration of hGH to a patient with serious cerebral injury undergoing hypothermia treatment resulted in the recovery of the immune function and a great improvement of resuscitation limit of the patient.

Thus, the present invention provides a medicament to be used supportively in a hypothermia treatment which contains human growth hormone (hGH) as an active ingredient.

The present invention for the first time discloses that the use of human growth hormone (hGH) is clinically effective for the prevention of damages associated with hypothermia treatment.

The term "medicament used supportively" as used herein refers to a medicine which is used supportively for the purpose of carrying out the hypothermia treatment safely and effectively, while avoiding the suppression of immune function or induction of infectious diseases which could occur in relation to the treatment.

The medicament of the present invention is applicable to any kinds of hypothermia treatment, but can be preferably used in a treatment for preventing the cerebral perfusion of a patient with serious cerebral injury.

The medicament of the present invention can be used more preferably in a mild hypothermia treatment conducted while controlling the cerebral temperature between 32 and 36° C.

The medicament of the present invention is especially preferred in a mild hypothermia treatment conducted while controlling the cerebral temperature between 32 and 33° C.

The medicament of the present invention exhibits immune function potentiation effect and/or microorganism infection inhibitory effect. Typical examples of microorganism infections include pneumonia and septicemia. The medicament of the present invention is especially suited to prevent pneumonia.

BEST EMBODIMENT FOR CARRING OUT THE INVENTION

Figure 1:
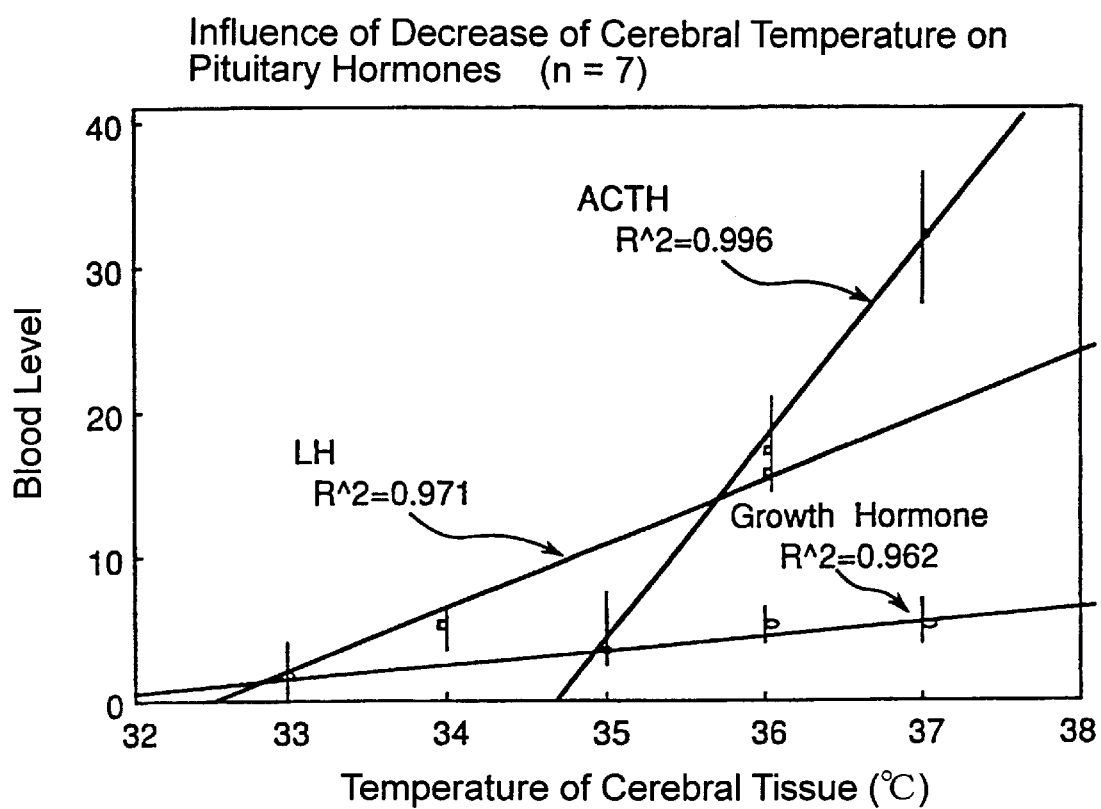
FIG. 1 is a graph showing the influence of the decrease of cerebral temperature on hGH secretion. In the figure, the horizontal and vertical axes represent the cerebral temperature and blood hGH level of the patient, respectively.

The present invention will be hereinafter described in more detail.

Human growth hormone (hGH) has been clinically used as a medicine in the treatment of pituitary dwarfism for almost 20 years, and various pharmaceutical preparations thereof are marketed. The medicament of the present invention can contain any one of available hGH preparations provided that it has an hGH activity. Mature hGH is preferred considering the antigenicity, or the like. However, a product purified from natural pituitary, Met hGH having methionine residue at the N-terminus, recombinant hGH and amino acid variants thereof also fall within the scope of the present invention on condition that they are pharmaceutical preparations having hGH activity.

The term "hGH activity" refers to an overall activity to promote the growth of every tissue but brain, especially bone, of a human mainly in the growth period. That is, it refers to all or a part the known physiological activities of hGH, for example, (1) growth promotion of bone or cartilage through the induction of somatomedin (IGF-I); (2) stimulation of amino acid uptake and protein synthesis and inhibition of protein decomposition; (3) acceleration of neutral lipid metabolism; (4) acceleration of sugar metabolism; (5) promotion of retention of electrolytes such as Na, K, etc. Currently, the hGH activity is widely put on the market on the basis of the international units (IU) and 1 mg recombinant hGH corresponds to about 3 units.

The medicament containing hGH of the present invention is not limited to any particular dosage form, but is preferred to be in the liquid or lyophilized form, in particular, for subcutaneous administration. The pharmaceutical compositions for parenteral administration may contain stabilizers or carriers known in the art, and are preferably in a form that can be used to prepare an isotonic solution before use. Examples of pharmaceutically acceptable carriers include plasma-derived proteins such as albumin, amino acids such as glycine and sugars such as mannitol. A nonionic surfactant such as polysorbate 80 or a pH regulator such as phosphate buffer may optionally be added. Such pharmaceutical compositions are described, for example, in Japanese Patent Publication (Kohyo) 3-503764. A lyophilized preparation for subcutaneous or intramuscular injection is generally used, and typical example includes "GENOTROPIN™ 16 IU" preparation for injection (Pharmacia Upjohn, Inc.) The mole ratio of a stabilizer to hGH in the medicament can be preferably 50–200 times for glycine, 700–3000 times for mannitol, and 0.7–30 times for polysorbate 80, in a buffer of preferably pH 4–8.

The medicament of the present invention may be left in a liquid form though, lyophilized form would be easier for handle.

Further, the medicament of the present invention may contain or be used in combination with antibacterial agents such as antibiotics or other immuno-activating agents provided that they do not affect the hGH activity. In particular, it appears that greater immune function maintaining effect could be achieved if, in combination with the medicament of the present invention, L-arginine (arginine hydrochloride, Morishita Roussel) or L-glutamine (Glumin, Kyowa Hakko Kogyo Co., Ltd.) capable of stimulating the hGH secretion is used in hypothermia treatment. There is no limitation about the dosage of L-arginine per hGH on condition that it is within the range sufficient for the stimulation of hGH secretion. It is known that hGH secretion can be stimulated without causing side effects when 0.5 g/5 ml/kg on average is administered as an intravenous drip for 30 minutes (Drugs in Japan, 1996, October, pp. 96, Ed., Japan Pharmaceutical Information Center, Yakugyo Jiho Co.,Ltd).

The term "a patient with serious cerebral injury" used herein in connection with the present invention means a patient in a serious state, especially, in a vital crisis condition, because of cerebral hemorrhage due to cerebral injury by accidents or subarachnoid hemorrhage, or ischemic cerebrovascular diseases such as cerebral infarction or cerebral embolism.

The term "hypothermia treatment" refers to a therapeutic method carried out to prevent an irreversible cranial nerve injury in the cases of accident or angiopathy, which is characterized in that a subject in anesthetized condition is cooled with a blanket having circulating cold water so that the temperature of the spinal cord and central nervous system is kept low for a particular period of time. Temperature in the hypothermia treatment is generally between 30 and 36° C.

Among hypothermia treatments, the "mild hypothermia treatment" conducted at cerebral temperature of between 32 and 36° C., slightly lower than normal cerebral temperature, is most preferred for the application of the medicament of the present invention, because one can expect the cerebral protection effect while arresting the invasion into whole body due to low temperature to the minimum extent. The cerebral temperature for the mild hypothermia treatment can be selected properly from two cases, i.e., one is 34–36° C. and the other is 32–33° C., depending on the condition of a patient or medical facilities. In the former case, the cerebral protection effect may be a little reduced but the invasion into whole body could be small. In the latter case, the opposite tendency can be seen.

The term "immune function" means a series of protective mechanism that acts on substances recognized to be extraneous and the self- and non-self recognition mechanism of a living body. Examples of foreign substances are, in general, microorganisms such as bacteria, fungi or virus, parasites, heterogeneous animal or plant, or protein or sugar chain or the like originated from cancer cells. Immunity can be divide broadly into two categories, that is, (a) humoral immunity wherein B lymphocytes produce antibodies capable of binding to an antigen and inactivate the antigenic protein, or cause phagocytosis by macrophages to devour antigenic bacteria; and (b) cellular immunity wherein T lymphocytes release activating factors (lymphokines) or attack antigens.

The term "immune function potentiation effect" in the present invention refers to a pharmacological action that enhances the immune function suppressed by hypothermia treatment. Especially, it refers to an activity to reinforce the cell-mediated immunity by increasing blood T cells recognized by cell surface antigens such as CD4 (helper/inducer T cell surface antigen) or CD8 (cytotoxic/suppressor T cell surface antigen).

The term "microorganism infection inhibitory effect" means an activity to inhibit or reduce microorganism-mediated infectious diseases which is caused by the suppression of immune function in a hypothermia treatment. Typical examples of microorganism infectious disease which can happen in a hypothermia treatment include pneumonia and septicemia.

The term "pneumonia prevention effect" means an activity to prevent or reduce the onset of pneumonia often caused by microorganism infection to a patient in immunosuppressed condition due to hypothermia treatment. There are many causative microorganisms of pneumonia, for example, bacteria (pneumococcus, Staphylococcus, hemolytic Streptococcus, influenza bacillus, *Pseudomonas aeruginosa*, etc.), virus (myxovirus, adenovirus, etc.), fungi (Candida, Aspergillus, Cryptococcus, etc.), mycoplasma and rickettsiae. The "pneumonia prevention effect", in relation to the present invention, means that it is possible to prevent or reduce the onset of pneumonia caused by any of these microorganisms.

The hGH containing medicament of the present invention can be administered subcutaneously, intravenously or intramuscularly, but the subcutaneous or intramuscular administration is generally employed. Although the dosage and times for the administration of hGH should be appropriately increased/decreased depending on the conditions, age, sex, or the like of the patient, hGH is normally administered at the dosage of about 0.5–50 U/day, preferably 2–20 U/day in the beginning of the hypothermia treatment. Generally, 1 to 5 times of administration of 8U hGH is sufficient to achieve the intended objective. When sufficient effect cannot be attained, the dosage or the number of administration may be increased.

The following Examples are provided to further illustrate the present invention.

TEST EXAMPLE 1
Decrease of hGH Secretion in Hypothermia Treatment

The hGH secretory function of a patient subjected to the hypothermia treatment was evaluated by measuring the blood hGH level. As shown in FIG. 1, the blood hGH concentration decreased almost linearly in proportion to the decrease of cerebral temperature in seven patients undergone the hypothermia treatment. The hGH secretion was almost zero at cerebral temperature of 32–33° C., where the mild hypothermia treatment can display the effect best.

These results show that the decrease of cerebral temperature causes the hGH depletion and also clarify the relation between the immunodeficiency condition and the decrease of hGH secretion in hypothermia treatment. These results also provide the theoretical grounds for the effectiveness of exogenous hGH on the immunodeficiency related to hypothermia treatment.

EXAMPLE 1
Lyophilized Preparation

Lyophilized preparation for subcutaneous or intramuscular administration, one of typical hGH containing medicaments of the present invention, can be prepared in the following manner.

To purified recombinant hGH (1 mg, about 3 units) are added glycine (0.34 mg), mannitol (9 mg) and non-ionic surfactant (polysorbate 80, 0.2 mg), and the mixture was dissolved in 1 ml phosphate buffer (pH 7.4, 5 mM). The solution was then lyophilize to obtain hGH preparation as a powder. The resultant medicament is used to prepare an isotonic solution before use.

EXAMPLE 2
Solution

Injectable solution for subcutaneous or intramuscular administration, one of typical hGH containing medicaments of the present invention, can be prepared in the following manner.

Purified recombinant hGH (5 mg, about 15 units) was dissolved in 1 ml citrate buffer (pH 6.0, 10 mM) containing 150 mM sodium chloride and 0.01% polysorbate 20. To the solution was added phenol (2.5 mg) to obtain injectable solution containing purified recombinant hGH.

Figure 2:
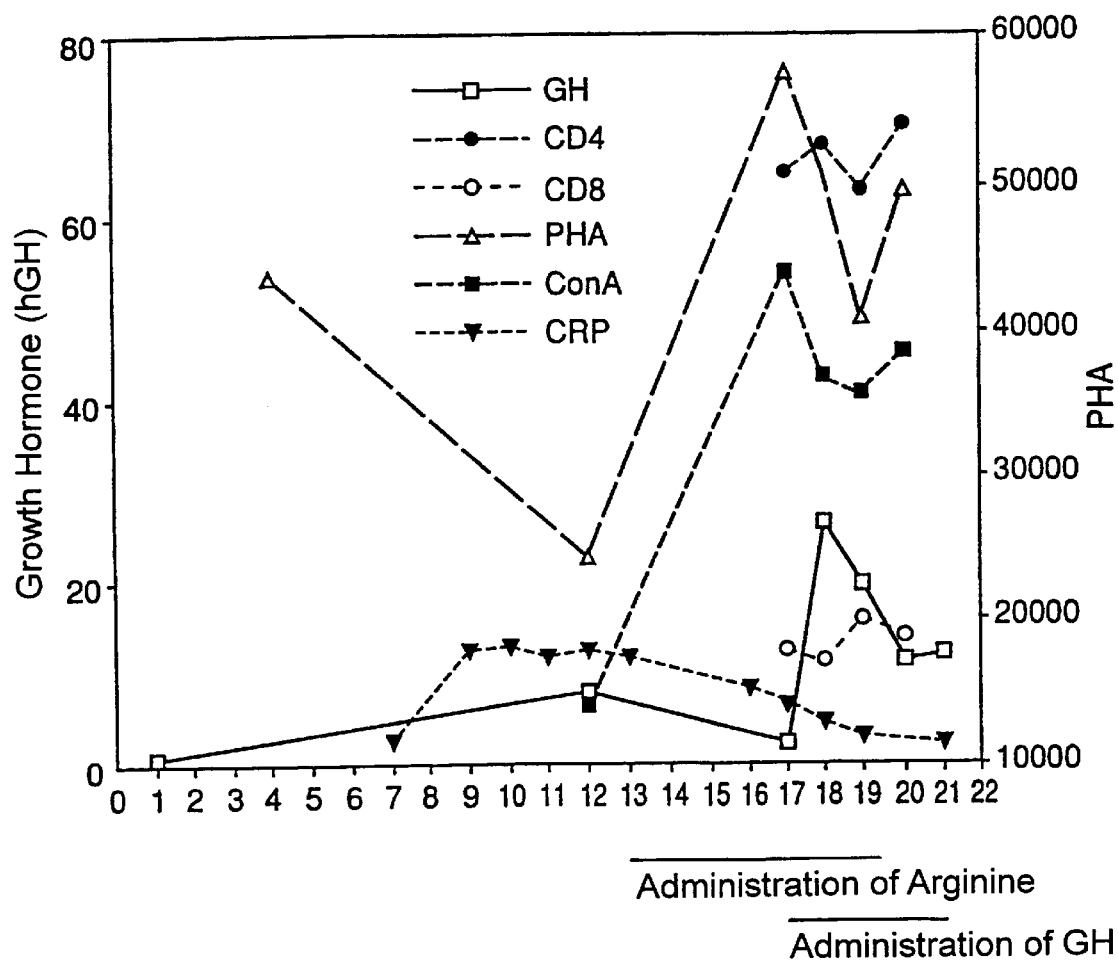
FIG. 2 is a graph showing the change of immune function of a patient who was treated by hypothermia with hGH administration. In the figure, the horizontal axis represents the number of days after the start. The vertical axis shows blood hGH concentration (□), PHA (△, index of lymphocyte blastogenesis), Con A (■, index of lymphocyte blastogenesis), CRP (▼, C reactive protein, index of inflammation), CD8 level (○, index of immune function), and CD4 level (●, index immune function).

EXAMPLE 3
Recovery of Immune Function in Patient Undergone Hypothermia Treatment Clinical experimental case: A patient (male, 58 years of age) with brain damage due to subarachnoid hemorrhage was hospitalized and treated by hypothermia treatment on the same day. The treatment was conducted for 22 days at cerebral temperature of 33 to 34° C., while administering an arginine solution (300 ml/day) from day 12 to 19, and hGH (GENOTROPIN™ 4 IU, Pharmacia Upjohn, Inc.) from day 17 to 21. The hGH (4 IU×2/day) was injected intramuscularly. Throughout the duration of the treatment, the blood level of CD4 and CD8 which are indices of immune function was measured in a conventional manner, and the attack of infectious diseases was monitored simultaneously. The results are shown in FIG. 2 As is apparent from FIG. 2, the concentration of both CD4 and CD8 as indices of immune function was maintained at normal level owing to the administration of hGH. Further, no infectious complications were observed during the hypothermia treatment and the patient made good progress.

Industrial Applicability

The medicament for hypothermia treatment of the present invention can inhibit the possible immunosuppression related to hypothermia treatment with which there have been no effective measures to cope, and prevent or reduce the occurrence of any infectious diseases. As a result, the present medicament allows the hypothermia treatment to exhibit fully the excellent clinical effects and makes it possible to save the life of a patient with seriously wounded brain damage, which otherwise has been impossible, whereby contributing to the development of medical treatment.

What is claimed is:

1. A method of treating a patient undergoing hypothermia treatment comprising administrating human growth hormone to the patient to prevent an infection or the suppression of immune function.

2. The method of claim 1, wherein the hypothermia treatment is given to prevent cerebral perfusion disturbance of a patient with serious cerebral injury.

3. The method of claim 1, wherein the hypothermia treatment is a mild hypothermia treatment conducted while controlling the cerebral temperature between 32–36° C.

4. The method of claim 1, wherein the hypothermia treatment is a mild hypothermia treatment conducted while controlling the cerebral temperature between 32–33° C.

5. The method of claim 2, wherein the hypothermia treatment is a mild hypothermia treatment conducted while controlling the cerebral temperature between 32–36° C.

6. The method of claim 2, wherein the hypothermia treatment is a mild hypothermia treatment conducted while controlling the cerebral temperature between 32–33° C.

7. The method of claim 1, wherein the infection is pneumonia.

8. A method for preventing the suppression of immune function of a patient undergoing a hypothermia treatment comprising administrating an effective amount of human growth hormone to the patient.

9. A method for preventing microorganism infection of a patient undergoing a hypothermia treatment comprising administrating an effective amount of human growth hormone to the said patient.

* * * * *